United States Patent
Wright et al.

(10) Patent No.: US 11,980,436 B2
(45) Date of Patent: May 14, 2024

(54) MEDICAL SYSTEM, METHOD AND COMPUTER PROGRAM

(71) Applicant: Sony Corporation, Tokyo (JP)

(72) Inventors: Christopher Wright, London (GB); Akinori Kamoda, Tokyo (JP)

(73) Assignee: Sony Corporation, Tokyo (JP)

(*) Notice: Subject to any disclaimer, the term of this patent is extended or adjusted under 35 U.S.C. 154(b) by 567 days.

(21) Appl. No.: 17/276,165

(22) PCT Filed: Sep. 25, 2019

(86) PCT No.: PCT/JP2019/037638
§ 371 (c)(1),
(2) Date: Mar. 15, 2021

(87) PCT Pub. No.: WO2020/075501
PCT Pub. Date: Apr. 16, 2020

(65) Prior Publication Data
US 2022/0031414 A1    Feb. 3, 2022

(30) Foreign Application Priority Data

Oct. 12, 2018  (EP) .................................... 18200255

(51) Int. Cl.
G06F 17/00   (2019.01)
A61B 34/00   (2016.01)
A61B 34/37   (2016.01)
B25J 9/16    (2006.01)

(52) U.S. Cl.
CPC .............. *A61B 34/76* (2016.02); *A61B 34/37* (2016.02); *B25J 9/1676* (2013.01)

(58) Field of Classification Search
CPC ........ A61B 34/76; A61B 34/37; B25J 9/1676; G16H 40/63
USPC .......................................................... 700/245
See application file for complete search history.

(56) References Cited

U.S. PATENT DOCUMENTS

| 10,081,107 | B2* | 9/2018  | Sakabe  | B25J 9/1697 |
| 10,310,608 | B1* | 6/2019  | Keller  | G06F 1/1694 |
| 10,328,576 | B2* | 6/2019  | Pinter  | B25J 9/1676 |
| 10,838,499 | B2* | 11/2020 | Wang    | G06F 3/0346 |
| 10,906,168 | B2* | 2/2021  | Kornbluh | G16Z 99/00 |
| 11,229,787 | B2* | 1/2022  | Daniels | H01B 13/00 |
| 11,416,076 | B2* | 8/2022  | Wang    | G06F 3/014 |

(Continued)

FOREIGN PATENT DOCUMENTS

| CN | 102323822 A | 1/2012 |
| CN | 104994805 A | 10/2015 |

(Continued)

OTHER PUBLICATIONS

Intuitive Spatial Tactile Feedback (Year: 2021).*

(Continued)

*Primary Examiner* — Ronnie M Mancho
(74) *Attorney, Agent, or Firm* — XSENSUS LLP

(57) ABSTRACT

A medical system is described in which, the system includes a control device having processing circuitry configured to: receive positional information relating to the position of at least a part of a surgical robot; determine a boundary around the surgical robot based on the positional information; and control the generation of a haptic sensation at the boundary.

20 Claims, 8 Drawing Sheets

(56) References Cited

U.S. PATENT DOCUMENTS

| | | | |
|---|---|---|---|
| 11,751,948 B2* | 9/2023 | Gregerson | A61B 34/76 606/185 |
| 2002/0120188 A1 | 8/2002 | Brock | |
| 2014/0207285 A1* | 7/2014 | Sakabe | B25J 9/1697 700/259 |
| 2015/0005785 A1 | 1/2015 | Olson | |
| 2016/0074123 A1 | 3/2016 | Bly | |
| 2016/0242858 A1 | 8/2016 | Moctezuma De La Barrera | |
| 2020/0353239 A1* | 11/2020 | Daniels | A61N 1/02 |
| 2021/0081048 A1* | 3/2021 | Sedal | G06F 3/016 |
| 2022/0288382 A1* | 9/2022 | Daniels | A61B 5/296 |

FOREIGN PATENT DOCUMENTS

| | | |
|---|---|---|
| CN | 105748026 A | 7/2016 |
| CN | 105939687 A | 9/2016 |
| CN | 107847283 A | 3/2018 |
| CN | 108472086 A | 8/2018 |
| WO | 2015/102964 A1 | 7/2015 |
| WO | WO-2017020081 A1 | 2/2017 |

OTHER PUBLICATIONS

Effective haptic feedback type for robot-mediated material discrimination depending on target properties (Year: 2023).*

Effective haptic feedback type for robot-mediated material discrimination depending on target properties (Year: 2023) (Year: 2023).*

International Search Report and Written Opinion dated Jan. 7, 2020, received for PCT Application PCT/JP2019/037638 Filed on Sep. 25, 2019, 13 pages.

Hamed et al., "Advances in Haptics, Tactile Sensing, and Manipulation for Robot-Assisted Minimally Invasive Surgery, Noninvasive Surgery, and Diagnosis", Journal of Robotics, Article ID 412816, 2012, pp. 1-14.

Georgilas et al., "Safe Human-Robot Interaction in Medical Robotics: A case study on Robotic Fracture Surgery System", Journal of Medical Robotics Research, vol. 2, No. 3, 2017, pp. 1-12.

Iwamoto et al., "Non-Contact Method for Producing Tactile Sensation Using Airborne Ultrasound", Haptics: Perception, Devices and Scenarios, Jun. 11, 2008, pp. 504-513.

Long et al., "Rendering Volumetric Haptic Shapes in Mid-Air Using Ultrasound", ACM Transactions on Graphics, vol. 33, No. 6, Article 181, Nov. 2014, pp. 1-10.

* cited by examiner

FIG. 2G

| Context Factors | | | | | | Barrier design functions 251 | | |
|---|---|---|---|---|---|---|---|---|
| Surgical stage as planned | Specific procedure B requiring close robot/human collaboration | Difficulty Rating <4 (moderate difficulty) | Difficulty Rating >8 (high difficulty) | Patient alarm Y is audible | Excessive bleeding | $f_u$ (Hz) | $d_b$ (cm) | $d_a$ (cm) |
| X | | X | | | | 50 | 30 | 35 |
| X | | | X | | | 100 | 25 | 30 |
| | | | | X | X | 300 | 10 | 15 |
| X | X | | | | | 100 | 20 | 25 |

252, 253, 254, 255

$f_u$ = frequency of ultrasound (barrier strength)

$d_b$ = barrier depth (distance from robot to edge of haptic barrier)

$d_a$ = barrier depth from active tool (distance from rotating or sharp robot attachment to edge of haptic barrier)

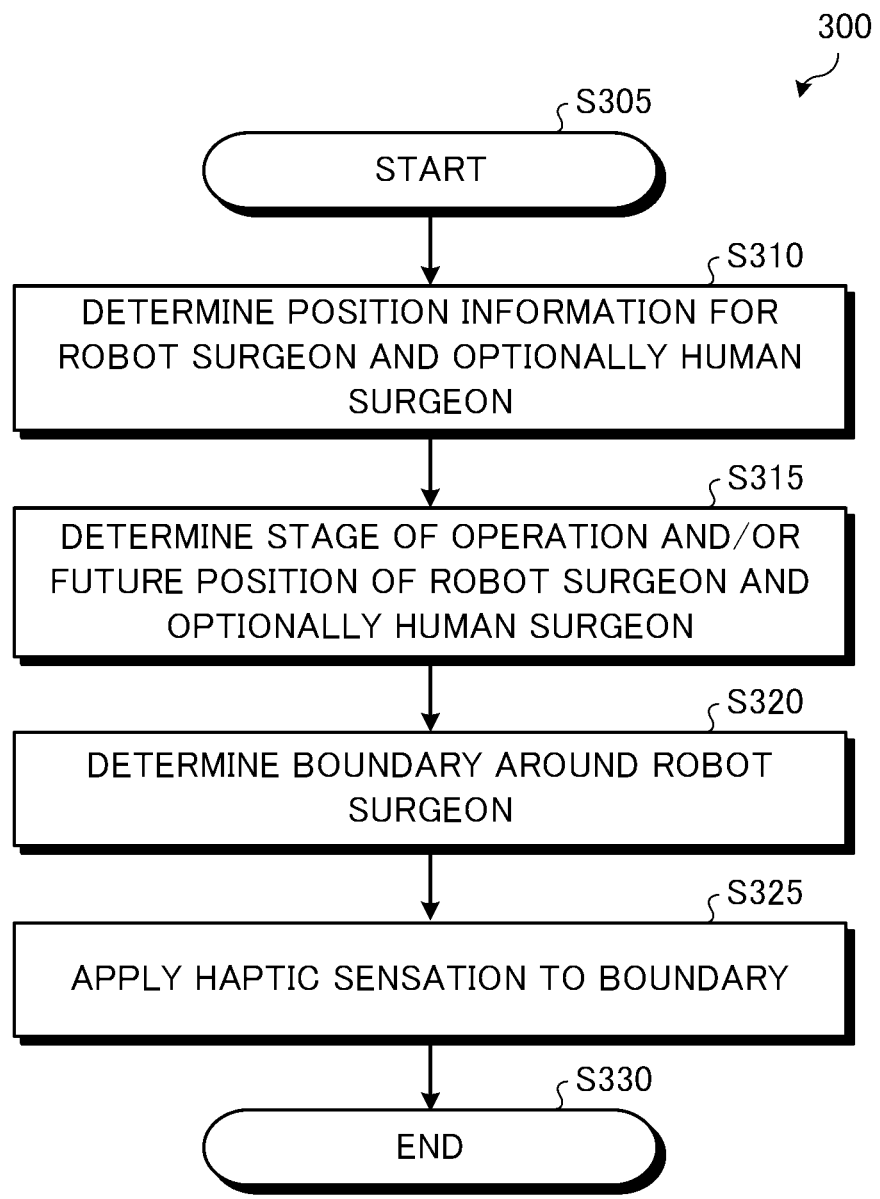

MEDICAL SYSTEM, METHOD AND COMPUTER PROGRAM

CROSS-REFERENCE TO RELATED APPLICATIONS

The present application is based on PCT filing PCT/JP2019/037638, filed Sep. 25, 2019, which claims priority to EP 18200255.0, filed Oct. 12, 2018, the entire contents of each are incorporated herein by reference.

TECHNICAL FIELD

The present disclosure relates to a medical system, method and computer program.

BACKGROUND

The "background" description provided herein is for the purpose of generally presenting the context of the disclosure. Work of the presently named inventors, to the extent it is described in the background section, as well as aspects of the description which may not otherwise qualify as prior art at the time of filing, are neither expressly or impliedly admitted as prior art against the present disclosure.

Collaborative robots, or "cobots" are designed not to replace human operators (surgeon(s) or a surgical team, for example), but to work with them in such a way as to utilise the differing skills of both the human and robot. Cobot systems have implications for surgery, where human-controlled robots are currently used for minimally invasive surgeries and autonomous systems are expected to become more common in the future.

Various risks must be accounted for when robots and humans work in close proximity with each other. Collisions between the two can cause injury to the human and trigger the robot's emergency stop mechanisms. The emergency stop mechanism in surgical robots can also be triggered by excessively close proximity or unexpected movement of the robot arms (which may potentially result from a human collision). While such mechanisms are an important safety feature, their use may cause delays to the task at hand (surgical or otherwise) and pose unnecessary risk to the patient.

Communication between an autonomous or semi-autonomous robot system and a human surgeon may also be problematic as both the human surgeon and the surgical robot may have various planned actions during the surgery but may struggle to identify the intentions of the other. This bi-directional intent recognition is an issue in facilitating a comfortable and effective working environment for both the surgical robot and the human surgeon, and necessitates the development of a communication system through which a surgical robot may indicate its future movements in a way that will not distract or be ignored by the surgeon.

From the above, it is apparent that a number of problems exist. Firstly, given that a collision between the human surgeon and the surgical robot may cause injury to a patient or slow down a surgical procedure, there is a need to avoid such a collision. Secondly, there is a need to improve communication between a surgical robot and a human surgeon.

It is also necessary that in addressing these two problems, the human surgeon is not too distracted by any solution.

SUMMARY

According to embodiments of the disclosure, there is provided a medical system, the system including a control device having processing circuitry configured to: receive positional information relating to the position of at least a part of a surgical robot; determine a boundary around the surgical robot based on the positional information; and control the generation of a haptic sensation at the boundary.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF DRAWINGS

A more complete appreciation of the disclosure and many of the attendant advantages thereof will be readily obtained as the same becomes better understood by reference to the following detailed description when considered in connection with the accompanying drawings, wherein:

FIG. 2G shows a detailed table explaining the embodiments of the disclosure.

FIG. 3 shows a flow chart carried out by the processing circuitry according to embodiments of the disclosure.

DESCRIPTION OF EMBODIMENTS

Figure 1:
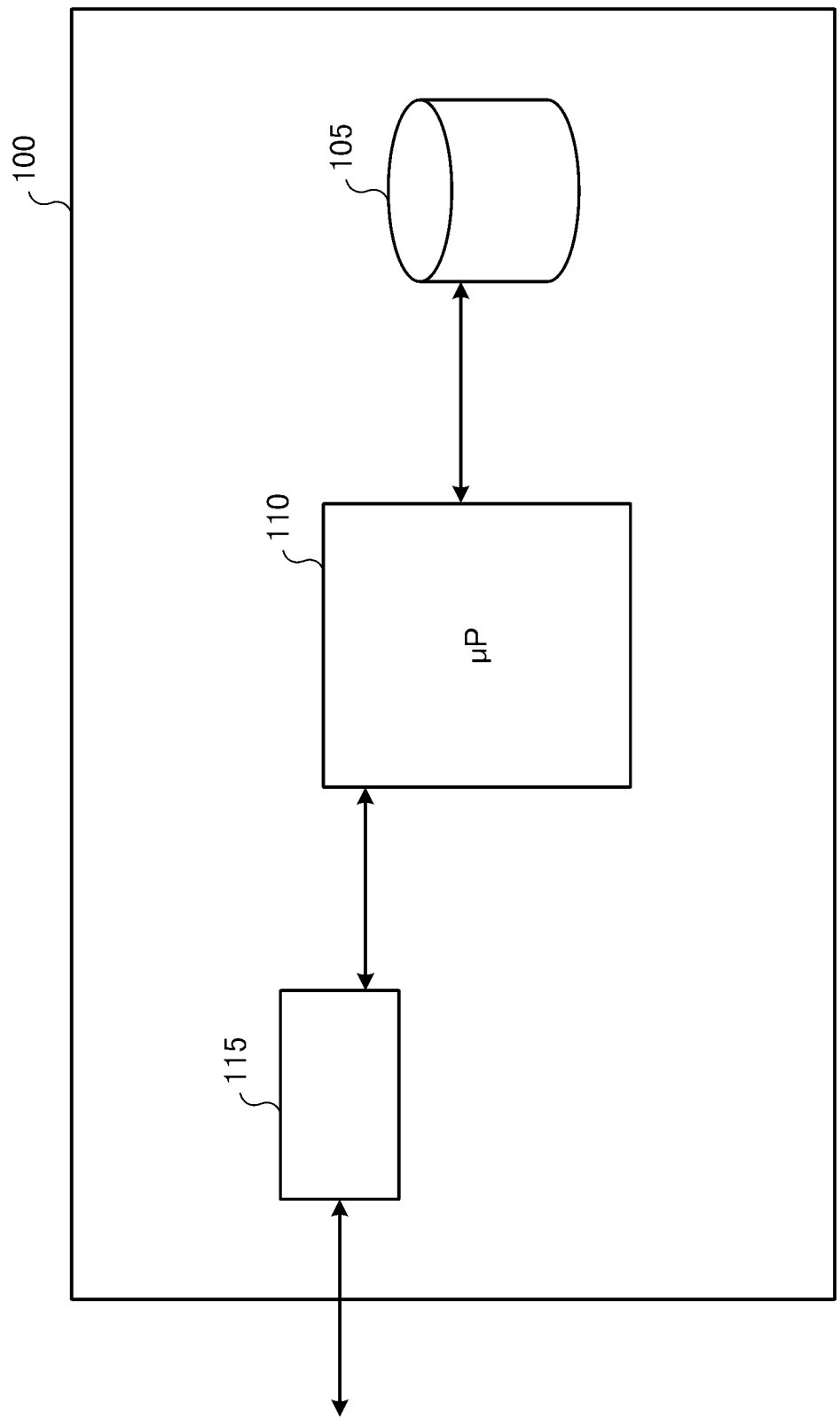
FIG. 1 shows a block diagram of a control device 100 used in a medical system according to embodiments of the disclosure.

Referring now to the drawings, wherein like reference numerals designate identical or corresponding parts throughout the several views.

FIG. 1 shows a block diagram of a control device 100 used in a medical system according to embodiments of the disclosure. The control device 100 aims to address the problems identified above. The control device 100 includes a control processor 110 (hereinafter called processing circuitry). The processing circuitry 110 is typically embodied as processor circuitry such as a microprocessor which is configured to operate using computer readable code. The processing circuitry 110 controls the operation of the control device 100 using the computer readable code. Of course, the processing circuitry 110 may be embodied as hardware (such as an Application Specific Integrated Circuit, Field Programmable Gate Array (FPGA) or the like).

Additionally connected to the processing circuitry 110 is control device storage 105. The control device storage 105 is a computer readable storage medium (such as an optically readable, magnetically readable or solid state). The control device storage 105 is configured to store the computer readable code using which the processing circuitry 110 operates. In addition, user profiles and various data structures are stored in the processing circuitry 110. In embodiments, the data structures may include one or more databases for different surgical procedures, different surgical devices or different surgeons as will be explained later.

Additionally connected to the processing circuitry 110 is control device communication circuitry 115. The control device communication circuitry 115 is configured to communicate with other devices which may be located within the operating room. This communication may be over a wired network (such as an Ethernet network) or may be over a wireless network (such as a WiFi network). The purpose of the control device communication circuitry 115 is to provide data to and receive data from the other devices within the operating room 100 as will become apparent. Moreover, the control device communication circuitry 115 may communicate with a centralised data system of a medical facility where information relating to surgical procedures, surgeon profiles and preferences, or surgical device parameters may be stored.

Figure 2A:
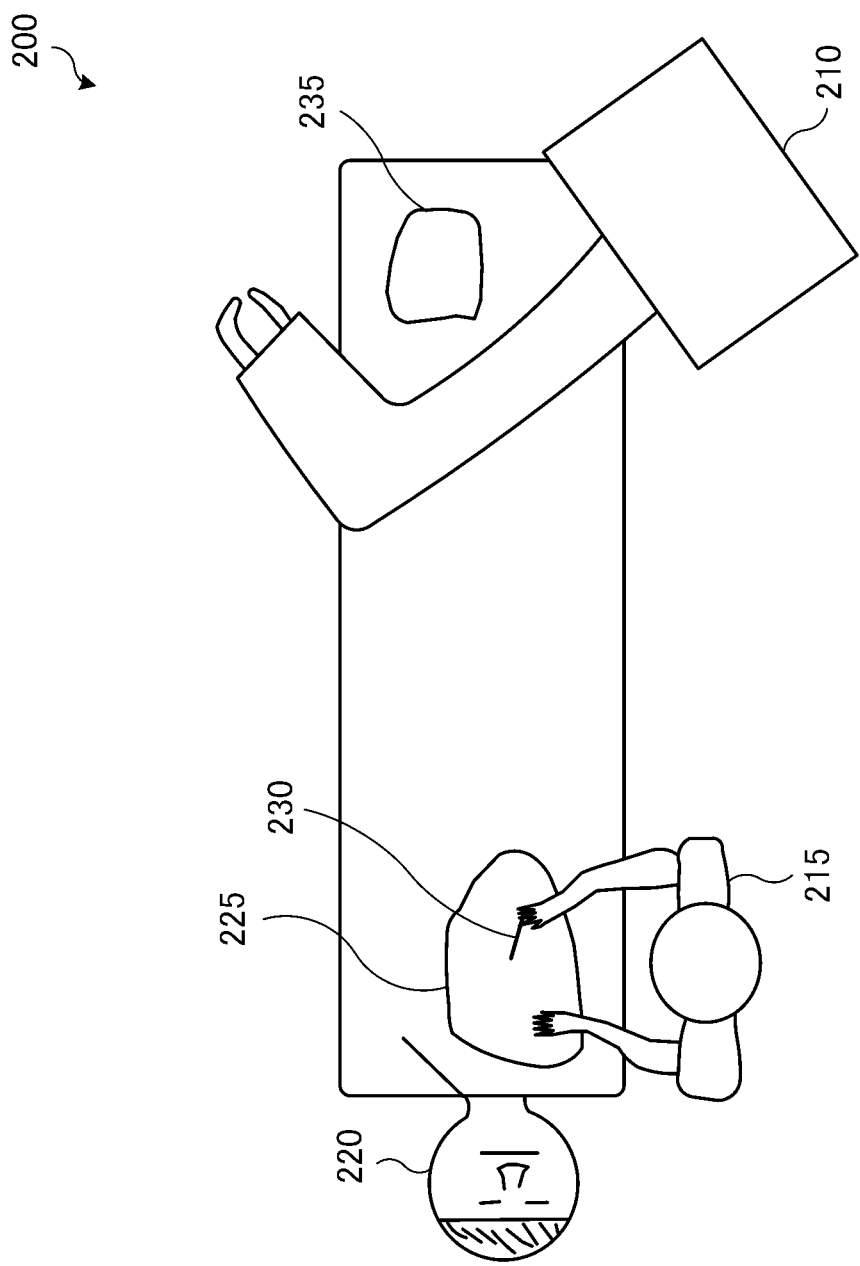
FIG. 2A shows a plan view 200 of a surgical robot 210 assisting a human surgeon 215 during a surgical procedure.

FIG. 2A shows a plan view 200 of a surgical robot 210 assisting a human surgeon 215 during a surgical procedure. FIG. 2 shows a patient 220 lying on a surgical table covered with a drape. The drape has a first cut-out section 225 and a second cut-out section 235. In the example embodiment of FIG. 2, the human surgeon 215 is operating on the patient 220 via the first cut-out section 225 using a scalpel 230. The surgical robot 210 is operating on a different part of the patient via the second cut-out 235. Although the human surgeon 215 and the surgical robot 210 are operating on different parts of the patient 215, it will be apparent that the human surgeon 215 and the surgical robot 210 may collide if, for example, the surgical robot 210 moves its arm during the procedure. This may pose a risk for the human surgeon but may be very dangerous for the patient 215 as the scalpel 230 may be knocked by such a collision causing injury or even death for the patient 215.

Figure 2B:
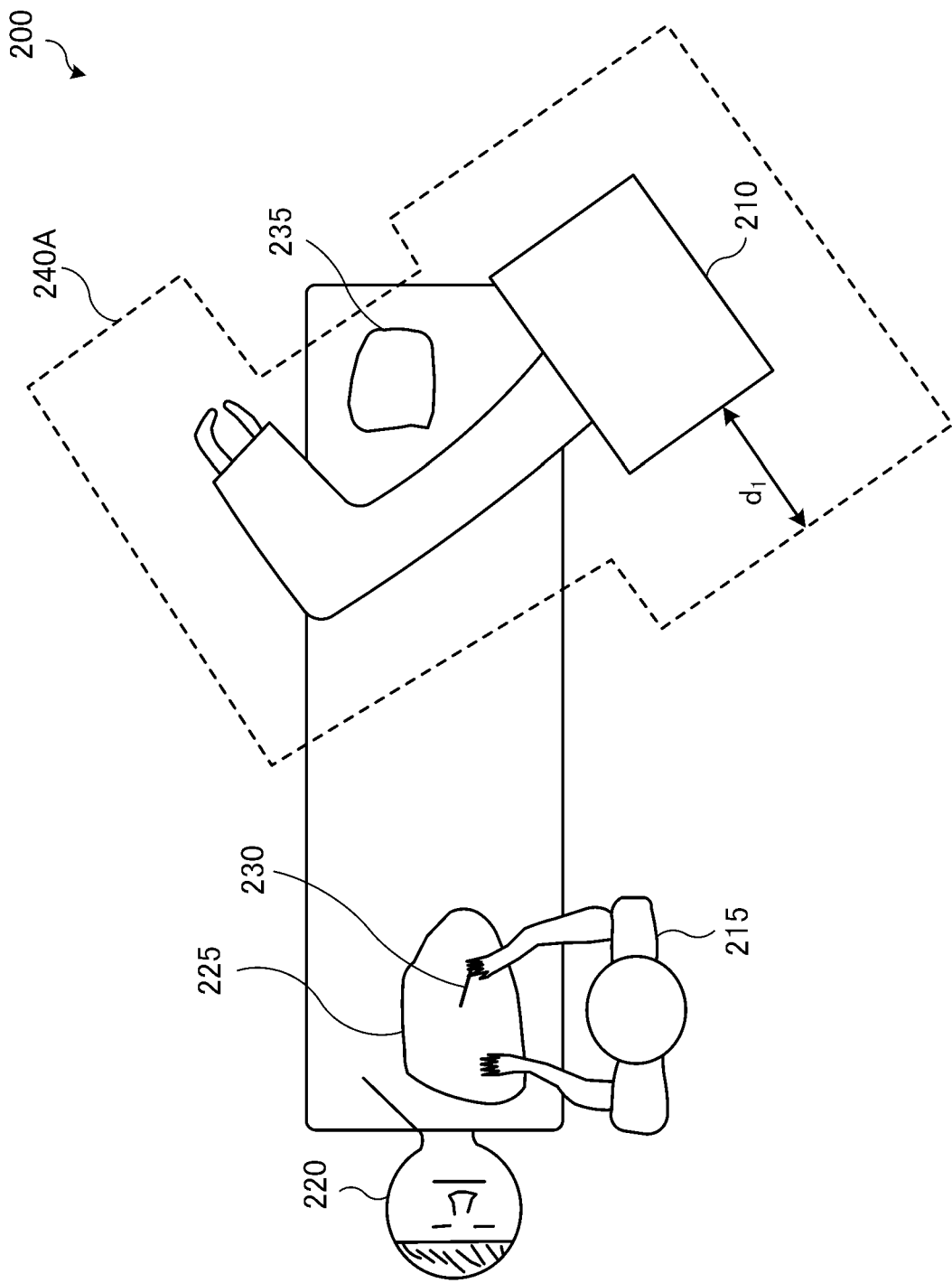
FIG. 2B shows the plan view of FIG. 2A is shown with a boundary 240A applied around the surgical robot 210.

Referring to FIG. 2B, the plan view of FIG. 2A is shown with a boundary 240A applied around the surgical robot 210. As all the other reference numerals refer to like features, for brevity, the explanation will be omitted.

The boundary 240A (sometimes referred to as a "boundary edge") is located a distance $d_1$ from the surgical robot 210. The purpose of the boundary 240A is to provide an alert to the human surgeon (or other member of the surgical team, which may include other robotic members) should that member of the surgical team cross that boundary 240A.

It should be noted that although FIG. 2B shows a uniform boundary distance around the surgical robot 210, the disclosure is not so limited. For example, the boundary 240A may be non-uniformly applied around the surgical robot 210. Specifically, the boundary 240A be closer to the surgical robot 210 for stationary parts of the surgical robot 210 (such as the main body of the surgical robot 210). Alternatively or additionally, the boundary 240A may be further from active parts of the surgical robot 210 or where there is a risk to the patient 225 should a collision occur. For example, the boundary 240A may be further from the surgical arm as this is more likely to move during the surgical procedure and is more likely cause injury to the patient should a collision occur. By increasing the distance of the boundary $d_1$ for the surgical arm, the member of the surgical team will receive an alert a long time before a collision will occur, thus reducing the likelihood of the collision taking place. It should also be noted that the boundary may be shaped to take account of a future movement or direction of movement of the surgical robot 210. This future movement may be the movement in the near future, for example, within the next 5 seconds or any other predetermined period of time. This shape may be non-uniformly designed.

The aim of the boundary that defines the location of the haptic barrier is to provide the member of the surgical team with an early warning system as their proximity to the current position of the surgical robot 210 increases. The boundary signifies a safe minimum distance which should be maintained from the surgical robot 210. The haptic barrier allows the member of the surgical team to move out of the way of the surgical robot 210. It may also provide a greater awareness of the movement of the surgical robot 210 without requiring a visual check.

In order to define the boundary, the position of the surgical robot 210 will need to be established. This is described later. Of course, the disclosure is not so limited. In instances, the position of the surgical robot 210 may not need to be established and the boundary may be applied by one or more devices attached to the surgical robot 210 (for example a ranged haptic device attached to the surgical robot 210). Therefore, as the position of the surgical robot 210 changes, the position of the boundary changes accordingly.

Figure 2C:
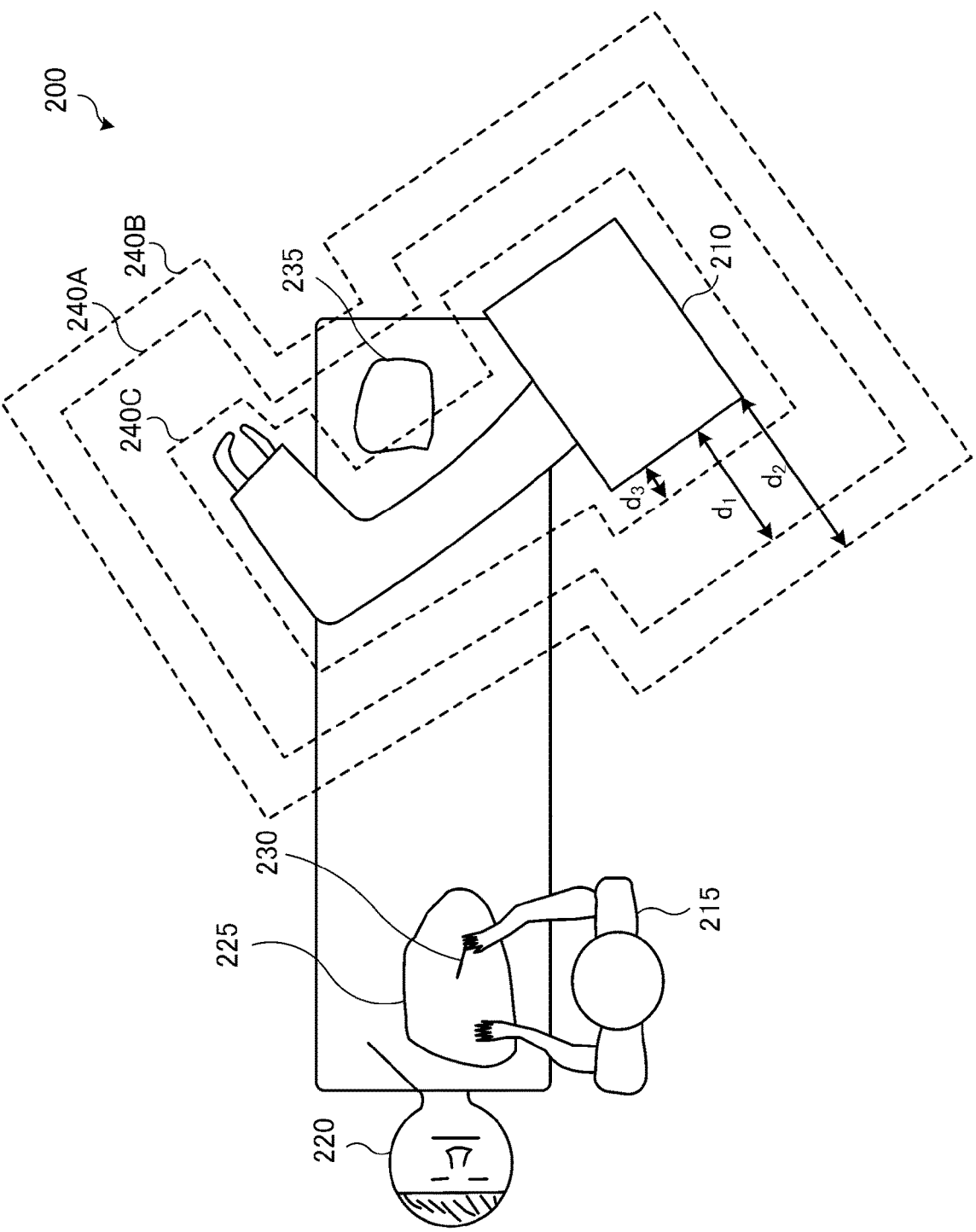
FIG. 2C shows embodiments of the present disclosure.

Referring to FIG. 2C, embodiments of the present disclosure are shown. In addition to the boundary 240A a distance $d_1$ from the surgical robot 210, a second boundary 240B a distance $d_2$ from the surgical robot 210 and a third boundary 240C a distance $d_3$ from the surgical robot 210 are defined. This provides a multi-layer haptic barrier such that the member of the surgical team may receive multiple staggered warnings based on their proximity to the surgical robot 210.

As will be apparent, the distance $d_2$ is larger than distance $d_1$ and the distance $d_3$ is smaller than distance $d_1$. Accordingly, a member of the surgical team would encounter the second boundary 240B, the boundary 240A and then the third boundary 240C before colliding with the surgical robot 210.

By providing a plurality of boundaries at different distances from the surgical robot 210, the likelihood of a member of the surgical team colliding with the surgical robot is reduced as the member of the surgical team will be notified of the risk of collision.

Figure 2D:
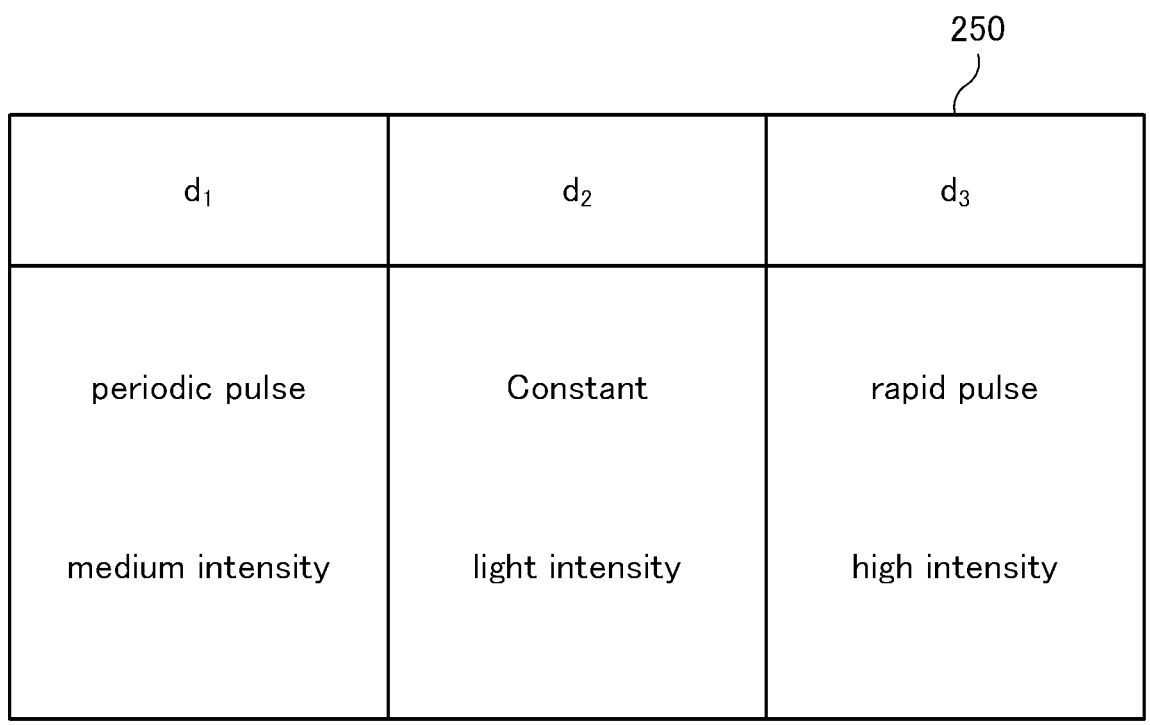
FIG. 2D shows a table according to embodiments of the disclosure.

Moreover, as will be apparent from FIG. 2D, the plurality of different boundaries may have a different associated haptic sensation. For example, a table 250 is shown with exemplary embodiments.

A further table 251 is shown in FIG. 2G which provides more information pertaining to the stage of surgery and the haptic barrier design. For example, where the surgical stage is as planned, but that stage is of moderate difficulty, the haptic barrier will have the characteristics of row 252. Where the surgical stage is as planned, but that stage is of high difficulty, the haptic barrier will have characteristics of row 253 (i.e. the barrier strength will be higher than that of row 252). Where the patient alarm is sounding due to excessive bleeding, the haptic barrier will have the characteristics of row 253 with very high barrier strength and finally, where the surgical stage is progressing as planned, but there is required close robot and human collaboration, the characteristics of row 254 are provided to the haptic barrier. It will be noted that the distance of the haptic barrier to the surgical robot 210 varies depending upon the surgical stage and any other context characteristics of the surgery. For example, where there is an emergency situation, the barrier is made much closer to the surgical robot 210 to allow the surgeon maximum flexibility in surgery. However, where the surgery is being carried out as planned and the stage of surgery is of moderate difficulty, a larger distance between the surgeon and the surgical robot is provided.

At the second boundary 240B a distance $d_2$ from the surgical robot 210, a constant haptic sensation is provided.

This haptic sensation has light intensity. This indicates to the member of surgical team that they are approaching the surgical robot 210 and are closer than the preferred safe distance from the surgical robot 210. The light intensity is the least distracting for the member of the surgical team. Moreover, providing a constant sensation is also less distracting for the member of the surgical team.

As the distance between the surgical robot 210 and the member of the surgical team reduces, the likelihood of a collision increases. Therefore, at the boundary 240A a distance $d_1$ from the surgical robot 210, a periodic pulse sensation is provided. The haptic sensation has a medium intensity. This indicates to the member of the surgical team that they are approaching the surgical robot 210 and that they are moving closer towards the surgical robot 210. The medium intensity is more distracting than the light intensity, as the likelihood of a collision is increased and so the member of the surgical team needs to be made more aware of the increased risk.

As the distance between the surgical robot 210 and the member of the surgical team reduces further, the likelihood of a collision increases further. Therefore, at the third boundary 240C a distance d3 from the surgical robot 210, a rapid pulse sensation is provided. The rapid pulse haptic sensation has high intensity. This indicates to the member of the surgical team that they are approaching the surgical robot 210 and that they are moving very close to the surgical robot 210. The high intensity haptic sensation is the most distracting as the likelihood of a collision is high and the member of the surgical team needs to be made more aware of the risk of collision.

Figure 2E:
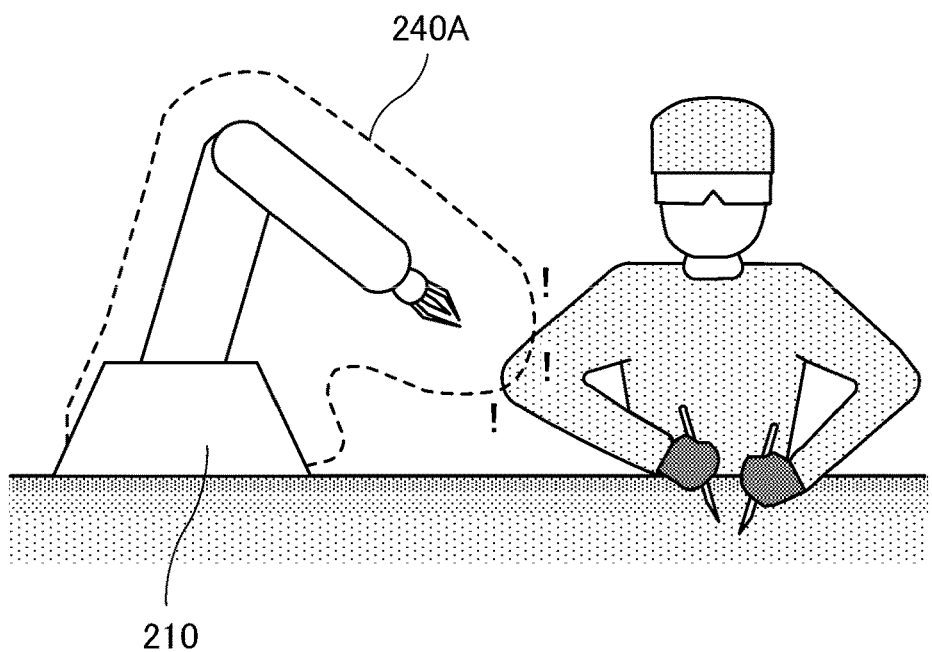
FIG. 2E shows a side view of a boundary.
Figure 2F:
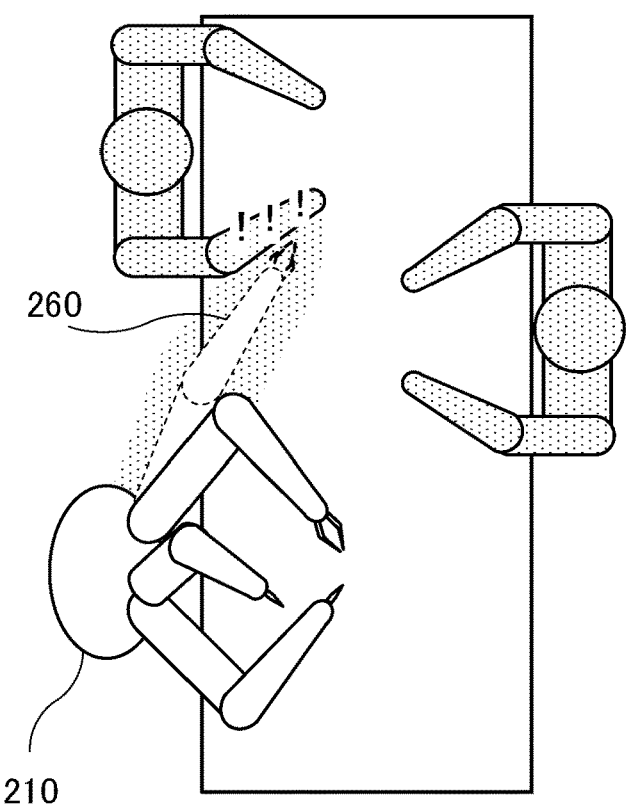
FIG. 2F shows a plan view explaining predicted future movement of the surgical robot.

Embodiments according to the disclosure are also shown in FIGS. 2E and 2F. For example, in FIG. 2E a side view of a surgeon carrying out a surgical procedure is shown. This shows that the boundary 240A surrounds the surgical robot 210 in three-dimensional space. Accordingly, even when an object crosses the boundary in the vertical direction, a haptic sensation is felt by the object.

In FIG. 2F, a plan view further explaining the Predicted Future Position of the surgical robot 210 is shown. The will be explained later under the heading "Predicted Future Position".

Although the above describes different combinations of intensity and type of haptic sensation, the disclosure is not so limited. Indeed, different types of haptic sensation are envisaged, such as long pulses and short pulses possibly having varying periodicity. Different intensities of haptic sensation are also envisaged. The different types and/or intensities of haptic sensation may be based on the relative distance between the surgical robot and the boundary edge or any predetermined criterion.

Indeed, it is envisaged that other alerts may be provided to the user in addition to the haptic sensation. For example, a further alarm may sound or a visual alert may be provided when one or more of the boundaries are crossed by the member of the surgical team. Instances of a member of the surgical team crossing one or more of the boundaries may also be recorded. This may include details of which boundary was crossed and by which member of the surgical team. This information may be used for later analysis of surgical procedures. For example, if the boundaries are regularly crossed for a particular surgical procedure, then the position of the members of the surgical team and the surgical robot 210 may be changed.

Although three haptic barriers are described, the disclosure is not so limited. Any number of haptic barriers and associated boundaries are envisaged. Additionally, it is possible that for each haptic barrier a different haptic intensity is provided. This may therefore produce a haptic gradient with increasing intensity the closer the member of the surgical team is to the surgical robot 210. This is advantageous as it provides an indication to the member of the surgical team as to the distance from the surgical robot 210 without requiring a visual check.

The haptic sensation may be applied to the member of the surgical team using many known techniques. For example, the surgical team may wear a haptic sensor in a smartwatch or sewn into the fabric of surgical scrubs or the like. Pixelated wearables which are distributed across the body of the member of the surgical team (through clothing, temporary smart tattoos or some other means) that are able to sense position and apply haptic feedback when required are also envisaged.

In advantageous embodiments, ranged haptic devices such as ultrasound phased arrays generate haptic effects by activating many ultrasound transducers (speakers) in a highly controlled pattern, creating wave interference patterns of ultrasound in the air. The simplest case is a single point focus. A plurality of these interference patterns may be combined to create the haptic impressions of lines, surfaces, edges and 3D shapes. The strength of the effect is dependent on the frequency and travel distance of the ultrasound. Therefore, as the distance is increased, haptic sensation strength may be maintained by including more ultrasound speakers, thus creating a lower number of focal points. In the case of ultrasound phased arrays, the properties of the surgical scrubs may be taken into account when generating the ultrasound haptic feedback.

These ranged haptic devices may be located on the casing of a robot arm for example, or may be placed in a separate location, such as mounted on the operating table.

As noted above, it is necessary to establish the position of the surgical robot 210 (and optionally its various components such as the surgical arm, surgical equipment and the like) needs to be established. This may be achieved using numerous known techniques. For example, the position of the surgical robot may be established using position sensors located within, or mounted on, the surgical robot 210 which provides, for example, data relating to the movement of a robot arm joint such as position, angle, posture or the like. This may require a sensor to be embedded in, or attached to, the joint, tool attachment points or other rotating and/or moving sections of the surgical robot 210.

Other sensors may include accelerometers, rotary or angular encoders, potentiometers or the like.

In addition, it is possible that the position of the each member of the surgical team relative to the surgical robot 210 may be established. This position information may be achieved using a vision system attached to cameras within the operating room. The processing circuitry 110 may receive the images from the cameras and establish the position of the members of the surgical team and/or the surgical robot 210. Alternatively or additionally, the position of the members of the surgical team may be established by the processing circuitry 210 based on the reflections of the ambient Wi-Fi signals or the like using known techniques or by one or more members of the surgical team wearing sensors in a smartwatch or sewn into the fabric of the surgical scrubs.

Once the position of each member of the surgical team is established relative to the surgical robot 210, a user's sensitivity to the haptic feedback may also be taken into account. For example, for a first member of the surgical team, the haptic feedback may be perceived as of higher intensity than that perceived by a second member of the surgical team. This individual perception of haptic feedback may be taken into account when setting the intensity of the haptic feedback at each boundary. In other words, the processing circuitry 210 knows the relative position of the surgical robot 210 and each member of the surgical team. Accordingly, the processing circuitry 210 will determine the relative intensity of the haptic feedback at the boundary and may be set to be of a low intensity, medium intensity or high intensity for that particular member of the surgical team depending upon the sensitivity of that member to haptic sensations.

It is noted above that the position of the surgical robot 210 and optionally the position of one or more members of the surgical team is established. Specifically, it is envisaged that any one or more of the following positions are established at any given time.

Current surgical robot 210 location and/or position;
Current surgical robot 210 speed of movement, including differentiations between bulk unit speed and individual tool and/or attachment movements.
Current location(s) of one or more members of the surgical team in the room;
Current hand/arm movements of one or more members of the surgical team in the room;
Predicted future Robot Operator speed and position. This will be explained later.
Predicted future actions of one or members of the surgical team. This will be explained later.

<Predicted Future Position>

As noted above, it is possible to predict the future position of the surgical robot 210 and/or one or more members of the surgical team.

The future position of the surgical robot 210 and/or the one or more members of the surgical team will be determined by the type of surgical procedure being carried out and the current stage of the surgical procedure. In other words, for a particular stage of a particular surgical procedure, the surgical robot 210 and/or one or more members of the surgical team will move in a predictable manner based on past experience of the members of the surgical team or best practice in an operating room. Accordingly, once the particular stage of a particular surgical procedure has been established, the future position of the surgical robot 210 and/or members of the surgical team may be derived.

The boundary may be defined based upon a predicted position of one or more members of the surgical team. For example, in the instance that the surgical robot 210 is predicted to move, the boundary may change relative to this predicted movement. In other words, if the surgical robot 210 is predicted to move to the right by 15 cm, a new boundary will be provided at this future position a predetermined time (for example 5 seconds) before the surgical robot 210 moves. The haptic sensation for this new boundary will be different accordingly to indicate to the members of the surgical team that the surgical robot 210 is about to move into that space. This reduces the likelihood of collision as the members of the surgical team may move to accommodate the future position of the surgical robot 210.

This is shown diagrammatically in FIG. 2E where the upcoming movement of the arm of the surgical robot is shown in 260. This is applied prior to the actual movement of the surgical robot 210 into that space to reduce likelihood of a collision.

In a surgical procedure such as neurosurgery, for instance, the stages comprise: 1) Anesthesia induction stage; 2) Navigation stage; 3) Craniotomy stage; 4) Treatment stage; 5) Intraoperative diagnosis stage and 6) Cranium-closing stage.

It is possible to capture an image (or sequence of images) of the particular stage of the particular surgical procedure and comparing this with known actions and stages. This will establish the particular stage of the particular surgical procedure. The image may be obtained via operating theatre cameras, including both internal (i.e. endoscopic view of surgical stage) and room (i.e. overhead cameras monitoring actions within the operating theatre) camera feeds. The images captured may be compared with a database of images that are associated with specific stages of an operation to identify the current surgical context.

In addition, the current tool being used may indicate the current stage of the surgical procedure. For example, when a surgical saw is used in neurosurgery, the neurosurgery will be at the Craniotomy stage. This may be further established by analysing the current surgical actions using tool sensors (so as to identify when the tool is moved or activated, for example) or using camera feeds (so as to indicate when a certain tool is being used, for example).

It should be noted that the surgical robot 210 and the members of the surgical team may behave differently depending upon the health of the patient at any given time. For example, if the health of the patient declines during the surgery or if there is excessive bleeding, the surgical procedure may enter a critical phase. In addition or alternatively, different stages of surgery may be defined as critical, for example, implanting a transplant organ. Embodiments of the disclosure in such a critical situation will now be explained.

Firstly, the health of the patient is continually monitored during a surgical procedure. This monitoring may be carried out using medical devices to monitor the patient's health, wearable devices on one or more members of the surgical team or built into the surgical robot 210 or using a camera system installed in the operating room.

A situation may be defined as critical at a predefined stage of surgery or if patient's health deteriorates to a particular level and possibly an alarm is triggered.

In the instance of a critical situation, the members of the surgical team increase their levels of concentration. This means that the members of the surgical team are less sensitive to haptic sensations and are less concerned about obstructions by the surgical robot 210. Therefore, the intensity of haptic sensation may increase to counter this.

In addition, or alternatively, the boundary shape and size may change to accommodate the reduction in concern about obstructions. For example, the boundary provided around the surgical robot 210 may reduce. In other words, in the example of FIG. 2B, the value of d1 may reduce and in the example of FIG. 2C, the value of d3 may reduce and the boundary 240A and second boundary 240B may be reduced or removed altogether.

This has the advantage of reducing the likelihood of a collision in a critical phase of surgery whilst appreciating that members' of the surgical team concentrate harder during critical phases of surgery.

Referring to FIG. 3, a flow chart 300 describing embodiments of the disclosure carried out in the processing circuitry 110 is shown. The process starts in step 305. The process moves to step 310 where the position information of the surgical robot 210 and optionally one or more members of the surgical team are determined. The process moves to optional step 315 where the stage of the surgical procedure and/or the future position of one or more members of the surgical team is determined. The process then moves to step 320 where the boundary edge is determined. The process then moves to step 325 where the haptic sensation is applied at the boundary edge. The process then stops in step 330.

Although the foregoing has described that the boundary shape and size may change in a critical phase of surgery, the disclosure is not so limited. The boundary shape and/or size and the haptic sensation may change depending upon the complexity of the stage of the surgical procedure. In other words, different stages of a surgical procedure have different associated complexities. These complexities and associated movement of the members of a surgical team are well understood for any given surgical procedure. As already noted, the complexity and concentration of the members of the surgical team changes the sensitivity to haptic sensation and the concern about obstruction to the surgical robot 210. Therefore, the boundary shape and/or size and haptic sensation may change in dependence upon the complexity of the stage of the surgical procedure.

Although the above shows the surgical robot 210 as being a robot arm carrying out surgical actions independently or in collaboration with a surgeon and thus assisting in surgery, the disclosure is not so limited. The surgical robot 210 carries out a range of movements within the operating room and is in the same domain as the surgical team and may work collaboratively with the surgical team. For example, a surgical robot 210 may be a robot assistant, such as a robot nurse which might assist the surgeon during an operation but not carry out any surgical actions on the patient (for example by passing the surgeon a scalpel, holding a light/sensor/scanner in place for the surgeon or help move a patient), or a surgical robot platform for an Artificial Intelligence entity, or be a robotic porter system for transport of tools, transplant organs or the like.

Although the above explains that a boundary has a particular haptic sensation associated with it, the disclosure is not so limited. For example, the haptic sensations in areas which human members of the surgical team is likely to move rapidly or suddenly (for example, near their hand) may be made stronger.

Although the above explains that a boundary may exist around a surgical robot 210, the disclosure is not so limited. For example, in the case of the ultrasound phased arrays, only points of haptic sensations may be provided. The concentration of these points may be increased in areas where likely incursion of one or more members of the surgical team into the boundary will occur. For example, the distribution of the ultrasound array may be customised to match the robot component or region of the surgical robot 210 to which it is applied. For example, a low-density ultrasound array distribution may be applied to regions of the surgical robot 210 (such as the rear body casing) where a coarse haptic barrier is acceptable. An ultrasound array with a higher distribution density may be applied to other regions (such as in the vicinity of tool attachments) where a finer, more accurate haptic barrier may be required. In addition, the current distance and relative speed of the closest part of one of the members' of the surgical team at a pre-defined number of evenly spaced points along the surgical robot arm's length (e.g. 1 per 10 cm) is calculated. A pre-defined function may then be applied to calculate the optimal barrier location on the length of the surgical robot's arm.

As noted above, it is possible that the boundary is determined to protect an area where the robot is currently located or where the robot is predicted to move in to. However, the disclosure is not so limited. Indeed, two boundaries may be provided to identify both the area where the robot is currently located and where the robot is predicted to move in to. This may be achieved by having two sets of ranged haptic devices (one set for each boundary). However, this effect may also be achieved by having a single ranged haptic device.

In this instance, resources to each boundary may need to be shared and allocated accordingly. For example, interleaved points of haptic sensation may be provided. That is, on a first boundary, a point of haptic sensation will be provided at position n, n+2, n+4, n+6 and on a second boundary, a point of haptic sensation will be provided at position n+1, n+3, n+5 and so on. The amount of haptic sensation will be changed depending on whether the boundary (for example, the first boundary) indicates an area where the robot is currently located and (for example, the second boundary) where the robot is about to move in to. This type of arrangement is an example of sharing and allocating resources.

In embodiments, the size and/or shape of the boundary may be changed over time. This may be changed at a predefined time period or frequency or may be re-designed in response to a relevant stimulus. For example, as the surgical situation changes such that the patient condition worsens, the surgeon moves, the robot task changes or the like, this may provide relevant stimulus for the size and/or shape of the boundary to change. Of course, other aspects of the boundary may change such as the haptic sensation provided at the boundary may change.

It will be appreciated that the disclosure may be applied to any kind of surgical robot. For example, the surgical robot may be a fully autonomous surgical robot where the surgical robot is provided with a task and the robot performs the task without human intervention. However, the disclosure is not so limited. In some instances, the surgical robot may be partly autonomous and so will perform limited tasks autonomously and other tasks under the control of a surgeon. In other instances, the surgical robot may not be autonomous at all and may operate under the complete control of a human surgeon. For example, the surgical robot may work with the surgeon in a master-slave relationship such that the human surgeon completely controls the surgical robot. In this arrangement, it is typical that the human surgeon and the surgical robot are located close together. Therefore the provision of embodiments of the disclosure in this arrangement is particularly useful.

Obviously, numerous modifications and variations of the present disclosure are possible in light of the above teachings. It is therefore to be understood that within the scope of the appended claims, the disclosure may be practiced otherwise than as specifically described herein.

In so far as embodiments of the disclosure have been described as being implemented, at least in part, by software-controlled data processing apparatus, it will be appreciated that a non-transitory machine-readable medium carrying such software, such as an optical disk, a magnetic disk, semiconductor memory or the like, is also considered to represent an embodiment of the present disclosure.

It will be appreciated that the above description for clarity has described embodiments with reference to different functional units, circuitry and/or processors. However, it will be apparent that any suitable distribution of functionality between different functional units, circuitry and/or processors may be used without detracting from the embodiments.

Described embodiments may be implemented in any suitable form including hardware, software, firmware or any combination of these. Described embodiments may optionally be implemented at least partly as computer software running on one or more data processors and/or digital signal processors. The elements and components of any embodiment may be physically, functionally and logically implemented in any suitable way. Indeed the functionality may be implemented in a single unit, in a plurality of units or as part of other functional units. As such, the disclosed embodiments may be implemented in a single unit or may be physically and functionally distributed between different units, circuitry and/or processors.

Although the present disclosure has been described in connection with some embodiments, it is not intended to be limited to the specific form set forth herein. Additionally, although a feature may appear to be described in connection with particular embodiments, one skilled in the art would recognize that various features of the described embodiments may be combined in any manner suitable to implement the technique.

Embodiments of the disclosure can be defined according to the following numbered paragraphs.

(1)
A medical system, the system including a control device having processing circuitry configured to:
receive positional information relating to the position of at least a part of a surgical robot;
determine a boundary around the surgical robot based on the positional information; and
control the generation of a haptic sensation at the boundary.

(2)
A medical system according to paragraph (1), wherein positional information defines a predicted future position of the surgical robot.

(3)
A medical system according to paragraph (2), wherein the processing circuitry is configured to apply a first haptic sensation to the user at the boundary of the position of the surgical robot and a second, different, haptic sensation to the user at the boundary of the future position of the surgical robot.

(4)
A medical system according to any preceding paragraph wherein the processing circuitry is configured to:
determine the boundary in accordance with a surgical status.

(5)
A medical system according to paragraph (4), wherein the surgical status is at least one of the following: the stage of the surgical procedure being carried out; the allocation of surgical staff and the surgical devices being used.

(6)
A medical system according to paragraph (4), wherein the surgical status is the stage of the surgical procedure being carried out and the processing circuitry is configured to determine the stage of the surgical procedure based upon at least one of a captured image and the status of a surgical device.

(7)
A medical system according to any preceding paragraph, wherein the processing circuitry is configured to:
apply a haptic sensation whose strength is based on a predetermined criterion.

(8)
A medical system according to paragraph (7), wherein the predetermined criterion is the relative distance between the surgical robot and the boundary.

(9)
A medical system according to any one of paragraphs (1) to (6), wherein the processing circuitry is configured to: determine a second, different, boundary around the surgical robot based upon the positional information; and control the generation of a different haptic sensation at each boundary.

(10)
A medical system according to paragraph (9), wherein a different strength haptic sensation is provided at each boundary.

(11)
A medical system according to paragraph (10), wherein the strength of the haptic sensation at a first distance from the surgical robot is higher than the strength of the haptic sensation at a second distance from the surgical robot; the first distance being lower than the second distance.

(12)
A medical system according to any one of paragraphs (7) to (11), wherein the strength is determined by at least one of the frequency and amplitude of the haptic sensation.

(13)
A medical system according to any preceding paragraph, wherein the processing circuitry is configured to generate an alarm when a boundary is crossed by an object.

(14)
A medical system according to any preceding paragraph, including an ultrasound array connected to the control device, wherein the processing circuitry is configured to apply the haptic sensation at the boundary using the ultrasound array.

(15)
A medical system according to any preceding paragraph, wherein the processing circuitry is configured to control a wearable device to apply the haptic sensation at the boundary.

(16)
A medical system according to any preceding paragraph, wherein the processing circuitry is configured to determine the position based upon an image.

(17)
A method of controlling a medical system, the method including:
receiving positional information relating to the position of at least a part of a surgical robot;
determining a boundary around the surgical robot based on the positional information; and
controlling the generation of a haptic sensation at the boundary.

(18)
A method according to paragraph (17), wherein positional information defines a predicted future position of the surgical robot.

(19)
A method according to paragraph (18), including applying a first haptic sensation to the user at the boundary of the position of the surgical robot and a second, different, haptic sensation to the user at the boundary of the future position of the surgical robot.

(20)
A method according to any one of paragraphs (17) to (19) including:
determining the boundary in accordance with a surgical status.

(21)
A method according to paragraph (20), wherein the surgical status is at least one of the following: the stage of the surgical procedure being carried out; the allocation of surgical staff and the surgical devices being used.

(22)
A method according to paragraph (20), wherein the surgical status is the stage of the surgical procedure being carried out and the processing circuitry is configured to determine the stage of the surgical procedure based upon at least one of a captured image and the status of a surgical device.

(23)
A method according to any one of paragraphs (17) to (22), including:
applying a haptic sensation whose strength is based on a predetermined criterion.

(24)
A method according to paragraph (23), wherein the predetermined criterion is the relative distance between the surgical robot and the boundary.

(25)
A method according to any one of paragraphs (17) to (22), including: determining a second, different, boundary around the surgical robot based upon the positional information; and controlling the generation of a different haptic sensation at each boundary.

(26)
A method according to paragraph (25), wherein a different strength haptic sensation is provided at each boundary.

(27)
A method according to paragraph (26), wherein the strength of the haptic sensation at a first distance from the surgical robot is higher than the strength of the haptic sensation at a second distance from the surgical robot; the first distance being lower than the second distance.

(28)
A method according to any one of paragraphs (23) to (27), wherein the strength is determined by at least one of the frequency and amplitude of the haptic sensation.

(29)
A method according to any one of paragraphs (17) to (28), including: generating an alarm when a boundary is crossed by an object.

(30)
A method according to any one of paragraphs (17) to (29), including controlling an ultrasound array to apply the haptic sensation at the boundary.

(31)
A method according to any one of paragraphs (17) to (30), including controlling a wearable device to apply the haptic sensation at the boundary.

(32)
A method according to any one of paragraphs (17) to (31), including: determining the position based upon an image.

(33)
A computer program comprising computer readable instructions which, when loaded onto a computer, configures the computer to perform a method according to any one of paragraphs (17) to (32).

The invention claimed is:

1. A medical system, the system comprising a control device having processing circuitry configured to:
receive positional information relating to the position of at least a part of a surgical robot;
determine a boundary around the surgical robot based on the positional information; and
control the generation of a haptic sensation when a member of a surgical team is at the boundary.

2. A medical system according to claim 1, wherein positional information defines a predicted future position of the surgical robot.

3. A medical system according to claim 2, wherein the processing circuitry is configured to apply a first haptic sensation to the member of the surgical team user at the boundary of the position of the surgical robot and a second, different, haptic sensation to the member of the surgical team at the boundary of the future position of the surgical robot.

4. A medical system according to claim 1 wherein the processing circuitry is configured to:
determine the boundary in accordance with a surgical status.

5. A medical system according to claim 4, wherein the surgical status is at least one of the following: the stage of the surgical procedure being carried out; the allocation of surgical staff and the surgical devices being used.

6. A medical system according to claim 4, wherein the surgical status is the stage of the surgical procedure being carried out and the processing circuitry is configured to determine the stage of the surgical procedure based upon at least one of a captured image and the status of a surgical device.

7. A medical system according to claim 1, wherein the processing circuitry is configured to:
apply a haptic sensation whose strength is based on a predetermined criterion.

8. A medical system according to claim 7, wherein the predetermined criterion is the relative distance between the surgical robot and the boundary.

9. A medical system according to claim 1, wherein the processing circuitry is configured to: determine a second, different, boundary around the surgical robot based upon the positional information; and control the generation of a different haptic sensation at each boundary.

10. A medical system according to claim 9, wherein a different strength haptic sensation is provided at each boundary.

11. A medical system according to claim 10, wherein the strength of the haptic sensation at a first distance from the surgical robot is higher than the strength of the haptic sensation at a second distance from the surgical robot; the first distance being lower than the second distance.

12. A medical system according to claim 7, wherein the strength is determined by at least one of the frequency and amplitude of the haptic sensation.

13. A medical system according to claim 1, wherein the processing circuitry is configured to generate an alarm when a boundary is crossed by an object.

14. A medical system according to claim 1, comprising an ultrasound array connected to the control device, wherein the processing circuitry is configured to apply the haptic sensation at the boundary using the ultrasound array.

15. A medical system according to claim 1, wherein the processing circuitry is configured to control a wearable device to apply the haptic sensation at the boundary.

16. A medical system according to claim 1, wherein the processing circuitry is configured to determine the position based upon an image.

17. A method of controlling a medical system, the method comprising:
receiving positional information relating to the position of at least a part of a surgical robot;
determining a boundary around the surgical robot based on the positional information; and
controlling the generation of a haptic sensation when a member of a surgical team is at the boundary.

18. A computer program comprising computer readable instructions which, when loaded onto a computer, configures the computer to perform a method according to claim 17.

19. The method according to claim 17, wherein the boundary is non-uniform.

20. A medical system according to claim 1, wherein the boundary is non-uniform.

* * * * *